United States Patent
Gerrans (10) Patent No.: US 10,864,323 B2
(45) Date of Patent: Dec. 15, 2020

(54) MODULATED DRUG DELIVERY

(71) Applicant: Sanovas Intellectual Property, LLC, Reno, NV (US)

(72) Inventor: Lawrence J. Gerrans, San Anselmo, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 182 days.

(21) Appl. No.: 15/877,061

(22) Filed: Jan. 22, 2018

(65) Prior Publication Data
US 2018/0140773 A1    May 24, 2018

Related U.S. Application Data

(63) Continuation of application No. 15/841,183, filed on Dec. 13, 2017, now Pat. No. 10,342,962, and a
(Continued)

(51) Int. Cl.
*A61M 5/172*    (2006.01)
*A61M 25/10*    (2013.01)
(Continued)

(52) U.S. Cl.
CPC ......... *A61M 5/1723* (2013.01); *A61B 5/0215* (2013.01); *A61B 5/4839* (2013.01);
(Continued)

(58) Field of Classification Search
CPC ..... A61B 5/01; A61B 5/0215; A61B 5/02158; A61B 5/0285; A61B 5/03; A61B 5/032;
(Continued)

(56) References Cited

U.S. PATENT DOCUMENTS 3,720,199 A    3/1973    Rishton et al.
4,186,745 A    2/1980    Lewis et al.
(Continued)

FOREIGN PATENT DOCUMENTS

EP    0894507 A2    2/1999
EP    1913882 A1    4/2008
(Continued)

OTHER PUBLICATIONS

Altinoz, et al.; "Noscapine and Diltiazem Augment Taxol and Radiation-Induced S-Phase Arrest and Clonogenic Death of C6 Glioma in Vitro"; May 2006; Surgical Neurology; 65(5):478-84.

*Primary Examiner* — Jason E Flick
(74) *Attorney, Agent, or Firm* — Forge IP, PLLC (57) ABSTRACT

A method of delivering a therapeutic and/or diagnostic agent to tissue is provided including the steps of inserting a catheter into a bodily cavity, the catheter having a proximal balloon and a distal balloon, inflating the proximal and distal balloons to create a chamber between the proximal and distal balloons, delivering the therapeutic and/or diagnostic agent to the chamber, measuring fluid pressure in the chamber, measuring at least one fluid dynamic characteristic of a subject, and adjusting the delivery of the therapeutic and/or diagnostic agent based at least in part on the measured volumetric pressure in the chamber and the at least one fluid dynamic characteristic of the subject.

18 Claims, 3 Drawing Sheets

Related U.S. Application Data continuation of application No. 14/489,109, filed on Sep. 17, 2014, now abandoned, said application No. 15/841,183 is a continuation of application No. 14/033,181, filed on Sep. 20, 2013, now abandoned, which is a continuation of application No. 13/037,826, filed on Mar. 1, 2011, now Pat. No. 8,597,239.

(51) Int. Cl.
| | | |
|---|---|---|
| *A61B 5/00* | (2006.01) | |
| *A61M 5/168* | (2006.01) | |
| *A61B 5/0215* | (2006.01) | |
| *A61M 5/00* | (2006.01) | |
| *A61B 5/03* | (2006.01) | |
| *A61B 1/313* | (2006.01) | |
| *A61B 5/01* | (2006.01) | |
| *A61B 5/0285* | (2006.01) | |
| *A61B 5/06* | (2006.01) | |
| *A61M 25/00* | (2006.01) | |
| *A61B 1/00* | (2006.01) | |
| *A61B 1/06* | (2006.01) | |
| *A61B 1/04* | (2006.01) | |

(52) U.S. Cl.
CPC ....... *A61B 5/6853* (2013.01); *A61M 5/16854* (2013.01); *A61M 25/1011* (2013.01); *A61B 1/00172* (2013.01); *A61B 1/00183* (2013.01); *A61B 1/04* (2013.01); *A61B 1/06* (2013.01); *A61B 1/3137* (2013.01); *A61B 5/01* (2013.01); *A61B 5/0285* (2013.01); *A61B 5/02158* (2013.01); *A61B 5/03* (2013.01); *A61B 5/032* (2013.01); *A61B 5/065* (2013.01); *A61M 5/007* (2013.01); *A61M 5/16836* (2013.01); *A61M 2005/1726* (2013.01); *A61M 2025/0002* (2013.01); *A61M 2025/0003* (2013.01); *A61M 2025/105* (2013.01); *A61M 2025/1052* (2013.01); *A61M 2205/3306* (2013.01); *A61M 2205/3334* (2013.01); *A61M 2205/50* (2013.01); *A61M 2205/502* (2013.01); *A61M 2205/52* (2013.01); *A61M 2230/005* (2013.01); *A61M 2230/30* (2013.01); *A61M 2230/50* (2013.01)

(58) Field of Classification Search
CPC ..... A61B 5/065; A61B 5/4839; A61B 5/6853; A61M 2005/1726; A61M 2025/0002; A61M 2025/0003; A61M 2025/105; A61M 2025/1052; A61M 2205/3306; A61M 2205/3334; A61M 2205/50; A61M 2205/502; A61M 2205/52; A61M 2230/005; A61M 2230/30; A61M 2230/50; A61M 25/1011; A61M 5/007; A61M 5/16836; A61M 5/16854; A61M 5/1723
USPC ...................................... 604/96.01
See application file for complete search history.

(56) References Cited

U.S. PATENT DOCUMENTS

| | | | |
|---|---|---|---|
| 4,423,725 | A | 1/1984 | Baran et al. |
| 4,446,867 | A | 5/1984 | Leveen et al. |
| 4,636,195 | A | 1/1987 | Wolinsky |
| 4,773,899 | A | 9/1988 | Spears |
| 4,824,436 | A | 4/1989 | Wolinsky |
| 4,921,484 | A | 5/1990 | Hillstead |
| 4,994,033 | A | 2/1991 | Shockey et al. |
| 5,049,132 | A | 9/1991 | Shaffer et al. |
| 5,100,425 | A | 3/1992 | Fischell et al. |
| 5,196,017 | A | 3/1993 | Silva et al. |
| 5,304,121 | A | 4/1994 | Sahatjian |
| 5,336,234 | A | 8/1994 | Vigil et al. |
| 5,397,307 | A | 3/1995 | Goodin |
| 5,423,745 | A | 6/1995 | Todd et al. |
| 5,545,133 | A | 8/1996 | Burns et al. |
| 5,599,307 | A | 2/1997 | Bacher et al. |
| 5,611,775 | A | 3/1997 | Machold et al. |
| 5,647,847 | A | 7/1997 | Lafontaine et al. |
| 5,674,192 | A | 10/1997 | Sahatjian et al. |
| 5,707,352 | A | 1/1998 | Sekins et al. |
| 5,728,064 | A | 3/1998 | Burns et al. |
| 5,785,685 | A | 7/1998 | Kugler et al. |
| 5,833,644 | A | 11/1998 | Zadno-Azizi et al. |
| 5,868,708 | A | 2/1999 | Hart et al. |
| 5,873,852 | A | 2/1999 | Vigil et al. |
| 5,932,248 | A | 8/1999 | Chen et al. |
| 6,048,332 | A | 4/2000 | Duffy et al. |
| 6,129,705 | A | 10/2000 | Grantz |
| 6,149,596 | A | 11/2000 | Bancroft |
| 6,190,354 | B1 | 2/2001 | Sell et al. |
| 6,245,008 | B1 | 6/2001 | Leschinsky et al. |
| 6,248,092 | B1 | 6/2001 | Miraki et al. |
| 6,485,500 | B1 | 11/2002 | Kokish et al. |
| 6,544,221 | B1 | 4/2003 | Kokish et al. |
| 6,616,597 | B2 | 9/2003 | Schock et al. |
| 6,623,452 | B2 | 9/2003 | Chien et al. |
| 6,632,196 | B1 | 10/2003 | Houser |
| 6,685,648 | B2 | 2/2004 | Flaherty et al. |
| 6,733,459 | B1 | 5/2004 | Atsumi |
| 7,014,652 | B2 | 3/2006 | Cioanta et al. |
| 7,025,718 | B2 | 4/2006 | Williams |
| 7,047,058 | B1 | 5/2006 | Dvorsky et al. |
| 7,462,165 | B2 | 12/2008 | Ding et al. |
| 7,569,032 | B2 | 8/2009 | Naimark et al. |
| 7,611,484 | B2 | 11/2009 | Wellman et al. |
| 7,658,966 | B2 | 2/2010 | Kokish |
| 7,727,226 | B2 | 6/2010 | Chang et al. |
| 8,052,668 | B2 | 11/2011 | Sih |
| 8,226,601 | B2 | 7/2012 | Gunday et al. |
| 8,540,667 | B2 | 9/2013 | Gerrans et al. |
| 8,597,239 | B2 | 12/2013 | Gerrans et al. |
| 2002/0010418 | A1 | 1/2002 | Lary et al. |
| 2003/0114791 | A1 | 6/2003 | Rosenthal et al. |
| 2004/0059290 | A1 | 3/2004 | Palasis |
| 2004/0215140 | A1 | 10/2004 | Forman |
| 2005/0015049 | A1 | 1/2005 | Rioux et al. |
| 2005/0043894 | A1* | 2/2005 | Fernandez ........... A61B 5/0215 702/19 |
| 2006/0135984 | A1 | 6/2006 | Kramer et al. |
| 2006/0189930 | A1 | 8/2006 | Lary et al. |
| 2007/0027075 | A1 | 2/2007 | Smithrud |
| 2007/0060942 | A2 | 3/2007 | Zadno-Azizi |
| 2007/0073264 | A1 | 3/2007 | Stedman et al. |
| 2008/0039791 | A1 | 2/2008 | Abboud et al. |
| 2008/0051627 | A1 | 2/2008 | Raju |
| 2008/0171985 | A1 | 7/2008 | Karakoca |
| 2008/0208118 | A1 | 8/2008 | Goldman |
| 2008/0294228 | A1* | 11/2008 | Brooke ................. A61N 1/326 607/116 |
| 2008/0300571 | A1* | 12/2008 | LePivert ........... A61B 18/1492 604/503 |
| 2009/0227851 | A1* | 9/2009 | Radojicic ............... A61B 5/032 600/309 |
| 2009/0229374 | A1 | 9/2009 | Carlisle et al. |
| 2010/0074895 | A1 | 3/2010 | Petricoin, III et al. |
| 2010/0113939 | A1 | 5/2010 | Mashimo et al. |
| 2010/0121270 | A1 | 5/2010 | Gunday et al. |
| 2010/0145398 | A1 | 6/2010 | Li et al. |
| 2010/0280451 | A1 | 11/2010 | Teeslink et al. |
| 2010/0286467 | A1 | 11/2010 | Pesach et al. |
| 2011/0082427 | A1 | 4/2011 | Golzarian et al. |
| 2011/0152683 | A1 | 6/2011 | Gerrans et al. |

(56) References Cited

U.S. PATENT DOCUMENTS

2011/0218494 A1* 9/2011 Gerrans .............. A61M 25/1011
                                                           604/101.05
2011/0293629 A1   12/2011 Bastid et al.

FOREIGN PATENT DOCUMENTS

| WO | 9304727    A1 | 3/1993 |
| WO | 2006130326 A2 | 12/2006 |
| WO | 2009046206 A1 | 4/2009 |
| WO | 2009086269 A2 | 7/2009 |

* cited by examiner

MODULATED DRUG DELIVERY

FIELD OF THE INVENTION

The present invention relates to methods and systems for delivering therapeutic and diagnostic agents to specific locations within and adjacent to bodily tissues and cavities. More specifically, the invention relates to a system and method of delivery of diagnostic and/or therapeutic agents to bodily tissues and cavities, wherein the delivery of the agents is adjusted based on a measurement of at least one fluid dynamic characteristic of a subject.

BACKGROUND OF THE INVENTION

In diagnosing and treating diseases of various body cavities and organs, it is necessary to deliver diagnostic and/or therapeutic agents to the organs at specified locations. Most common routes of drug delivery include a non-invasive peroral (through the mouth), topical (skin), transmucosal (nasal, buccal/sublingual, vaginal, ocular and rectal) and inhalation routes. However, many therapeutic and diagnostic agents in general may not be delivered using these routes because they might be susceptible to enzymatic degradation or cannot be absorbed into the systemic circulation efficiently due to molecular size and charge issues, and thus, will not be fully therapeutically effective.

Because of that, many such drugs have to be delivered by injection. However, there are several known problems associated with the injection process. One of such problems is undesirable absorption of the diagnostic or therapeutic agents into tissue, which is particularly prevalent with intravenously injected agents. Once the intravenous absorption has occurred, damage can continue for months and involve nerves, tendons and joints. If treatment is delayed, surgical debridement, skin grafting, and even amputation have been known to be the unfortunate consequences. Undesirable absorption during intravenuous administration is a particularly significant problem with cytotoxic drugs used for treatment of cancer (i.e. during chemotherapy) because of high toxicity of such drugs.

Often, it is necessary to deliver medicinal or therapeutic substances to remote and not easily accessible blood vessels and other lumens within body organs, such as lungs. It is also important to be able to deliver defined doses of therapeutic and diagnostic substances directly into target tissue because such substances are often very expensive or are capable of causing serious harm if delivered in excess. Therefore, there is a need for systems and methods capable of delivering therapeutic and diagnostic agents directly to target tissue sites inside a patient's body.

However, the known drug delivery systems suffer from a number of disadvantages and shortcomings. For example, the prior art delivery systems are usually complex, bulky and difficult to introduce into remote locations within a patient's body, and are typically specifically designed for delivering drugs to particular body organs, and therefore, are unsuitable for use on a variety of internal organs and tissues. Additionally, the prior art devices are incapable of delivering therapeutic or medicinal fluids in precise quantities. Furthermore, known delivery devices do not take into consideration changing fluid dynamic characteristics of a patient to adjust the delivery of the agent accordingly. For example, it is important to take into account pressure of bodily fluids when delivering agents such that the agent can be delivered at a pressure that exceeds the pressure of a bodily fluid in order to facilitate absorption of the agent into target tissue.

In some applications, such as pulmonology, it is desirable to know the degree to which the lung is inflated at any given time in order to deliver a therapeutic and/or diagnostic agent at the right time. It is also desirable to measure other bodily fluid dynamic characteristics, such as fluid velocity, fluid density, and fluid temperature, and to modulate the delivery of the agents based on these characteristics.

What is desired, therefore, is an improved system and method of delivery of diagnostic and/or therapeutic agents to bodily tissues and cavities, wherein at least one fluid dynamic characteristic of a patent is monitored and measured, and the delivery of the agent is adjusted based on the at least one measured fluid dynamic characteristic of a patient to facilitate better absorption of the agent into target tissue.

SUMMARY OF THE INVENTION

In order to overcome the deficiencies of the prior art and to achieve at least some of the objects and advantages listed, the invention comprises a method of delivering a therapeutic and/or diagnostic agent to tissue, including the steps of inserting a catheter into a bodily cavity, the catheter having a proximal balloon and a distal balloon, inflating the proximal and distal balloons to create a chamber between the proximal and distal balloons, delivering the therapeutic and/or diagnostic agent to the chamber, measuring fluid pressure in the chamber, measuring at least one fluid dynamic characteristic of a subject, and adjusting the delivery of the therapeutic and/or diagnostic agent based at least in part on the measured volumetric pressure in the chamber and the at least one fluid dynamic characteristic of the subject.

In some embodiments, the at least one fluid dynamic characteristic of the subject is measured via at least one sensor positioned on the subject.

In certain embodiments, the at least one fluid dynamic characteristic of the subject includes at least one of fluid velocity, fluid pressure, fluid density, and fluid temperature.

In some embodiments, the at least one fluid dynamic characteristic of the subject includes at least one of a diastolic pressure and a systolic pressure.

In certain embodiments, the at least one fluid dynamic characteristic of the subject includes at least one of lymphatic fluid dynamic characteristic, blood dynamic characteristic, cerebrospinal fluid dynamic characteristic, interstitial fluid dynamic characteristic, and intracellular fluid dynamic characteristic.

In some cases, the step of adjusting the delivery of the therapeutic and/or diagnostic agent includes increasing or decreasing volumetric pressure inside the chamber. In certain of these cases, the step of decreasing volumetric pressure inside said chamber includes allowing fluid to escape said chamber via an outflow lumen. In additional of these cases, the catheter further includes a middle balloon positioned between the proximal and distal balloons, and the volumetric pressure inside the chamber is increased or decreased by adjusting the inflation of the middle balloon.

In some embodiments, the step of adjusting the delivery of the therapeutic and/or diagnostic agent includes increasing or decreasing pressure at which the agent is delivered to the chamber.

In some embodiments, the step of measuring fluid pressure in the chamber includes measuring pressure via at least one sensor positioned at a fluid source. In additional embodiments, the step of measuring volumetric pressure in the chamber includes measuring pressure via at least one sensor positioned inside the chamber. In yet further embodiments, the step of measuring volumetric pressure in the chamber includes measuring pressure via at least one sensor positioned in a catheter lumen.

A method of delivering a therapeutic and/or diagnostic agent to tissue is also provided, including the steps of inserting a catheter into a bodily cavity, delivering the therapeutic and/or diagnostic agent to tissue via the catheter, measuring pressure at which the therapeutic and/or diagnostic agent is delivered to tissue, measuring at least one fluid dynamic characteristic of a subject, and adjusting the delivery of the therapeutic and/or diagnostic agent based at least in part on the measured pressure of the agent and the at least one fluid dynamic characteristic of the subject.

In some embodiments, the at least one fluid dynamic characteristic of the subject is measured via at least one sensor positioned on the subject.

In certain embodiments, the at least one fluid dynamic characteristic of the subject includes at least one of fluid velocity, fluid pressure, fluid density, and fluid temperature. In additional embodiments, the at least one fluid dynamic characteristic of the subject includes at least one of a diastolic pressure and a systolic pressure. In further embodiments, the at least one fluid dynamic characteristic of the subject includes at least one of lymphatic fluid dynamic characteristic, blood dynamic characteristic, cerebrospinal fluid dynamic characteristic, interstitial fluid dynamic characteristic, and intracellular fluid dynamic characteristic.

In some cases, the step of adjusting the delivery of the therapeutic and/or diagnostic agent includes increasing or decreasing pressure at which the agent is delivered to tissue.

In certain embodiments, the step of measuring pressure at which the therapeutic and/or diagnostic agent is delivered to tissue includes measuring pressure via at least one sensor positioned at a fluid source. In additional embodiments, the step of measuring pressure at which the therapeutic and/or diagnostic agent is delivered to tissue includes measuring pressure via at least one sensor positioned in a catheter lumen.

A system for delivering a therapeutic and/or diagnostic agent to tissue is further provided, including a catheter having a delivery port and a lumen through which a therapeutic and/or diagnostic agent is communicated to the delivery port, at least one first sensor that measures pressure of the therapeutic and/or diagnostic agent being delivered via the port and generates a signal indicating the pressure, a processor that receives the signal from the at least one first sensor, and at least one second sensor that measures at least one fluid dynamic characteristic of a subject and transmits a signal indicating the at least one fluid dynamic characteristic to the processor, wherein the processor adjusts the delivery of the therapeutic and/or diagnostic agent based at least in part on the measured pressure of the agent and the at least one fluid dynamic characteristic of the subject.

In some embodiments, the at least one fluid dynamic characteristic of the subject includes at least one of fluid velocity, fluid pressure, fluid density, and fluid temperature. In additional embodiments, the at least one fluid dynamic characteristic of the subject includes at least one of a diastolic pressure and a systolic pressure. In further embodiments, the at least one fluid dynamic characteristic of the subject includes at least one of lymphatic fluid dynamic characteristic, blood dynamic characteristic, cerebrospinal fluid dynamic characteristic, interstitial fluid dynamic characteristic, and intracellular fluid dynamic characteristic.

In certain embodiments, the catheter further includes a fluid source and the at least one first sensor is positioned at a fluid source.

In some cases, the at least one first sensor is positioned in a catheter lumen.

In certain embodiments, the processor adjusts the delivery of the therapeutic and/or diagnostic agent by increasing or decreasing pressure at which the agent is delivered via the port.

In some embodiments, the catheter includes a proximal balloon and a distal balloon and a fluid source that inflates the proximal and distal balloons by supplying fluid thereto to create a chamber between the proximal and distal balloons, and the port is positioned between the proximal and distal balloons. In certain of these embodiments, the at least one first sensor is positioned inside the chamber between the proximal and distal balloons. In additional embodiments, the processor adjusts the delivery of the therapeutic and/or diagnostic agent by increasing or decreasing volumetric pressure inside the chamber. In yet further of these embodiments, the catheter also includes a middle balloon positioned between the proximal and distal balloons and the processor adjusts the delivery of the therapeutic and/or diagnostic agent by adjusting the inflation of the middle balloon.

In certain embodiments, the catheter further includes an outflow lumen that allows fluid to escape the chamber.

Other objects of the invention and its particular features and advantages will become more apparent from consideration of the following drawings and accompanying detailed description.

DETAILED DESCRIPTION OF THE INVENTION

Figure 1:
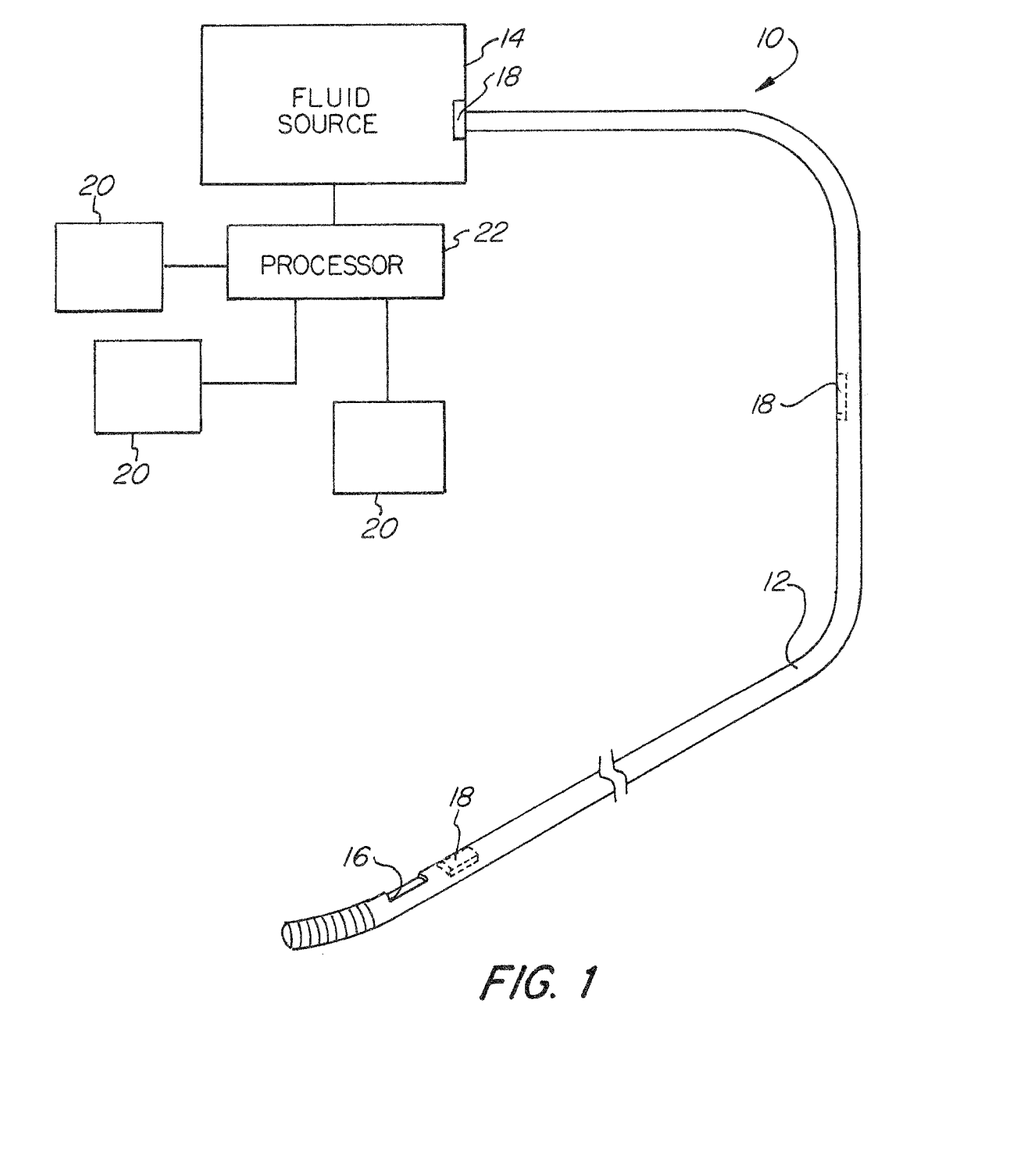
FIG. 1 is a schematic view of a system for delivering a therapeutic and/or diagnostic agent to tissue in accordance with the invention.

The basic components of one embodiment of a system for delivering a therapeutic and/or diagnostic agent to tissue in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As illustrated in FIG. 1, the system (10) for delivering a therapeutic and/or diagnostic agent to tissue includes a catheter (12) and a fluid source (14). The catheter (12) may have any suitable diameter and length depending on a particular application, and may be flexible, rigid or semi rigid. The catheter (12) may be made with any commercially available material, such as polyethylene, that is flexible enough to allow the shaft to be safely inserted through the available opening of a bodily cavity such that it will bend instead of puncturing the walls of the cavity, and at the same time is rigid enough such as it will maintain its shape as it is passed alongside and/or through the available opening of the bodily cavity. A distal end of the catheter (12) may include a safety tip (not shown) that, when the catheter (12) is inserted into a bodily cavity, will bend instead of puncturing the walls of the cavity.

Any suitable fluid source may be used in accordance with the present invention. In the embodiment shown in FIG. 1, the fluid source (14) is an electro-pneumatic pump having controls on the front thereof, from which a physician or assistant can control the system (as well as a remote control unit), such as that disclosed in U.S. Pat. No. 8,226,601 to Gunday et al., the specification of which is hereby incorporated by reference herein in its entirety. A proximal end of the catheter (12) is connected to the pump (14) via any suitable connection. The pump (14) supplies a fluid, such as a gas, liquid, or mixture thereof, to the catheter (12). The fluid may be used to inflate one or more inflatable balloons connected to the catheter (12), as shown in FIGS. 2 and 3A-3C. The fluid may also be the therapeutic and/or diagnostic agent that is supplied to tissue via a port (16) in the catheter. The pump (14) also includes a variety of capabilities, such as feedback measurements, proper inflation/deflation of the balloons and delivery of the agents, balloon identification and such, many details of which are described in U.S. Pat. No. 8,226,601 and also described in more detail below. In certain advantageous embodiments, the pump (14) further includes a vacuum source to evacuate fluid from the catheter (12).

The agent may be delivered to target tissue via any suitable agent delivery device. For example, the agent may be delivered directly via one or more openings (16) at the distal end of the catheter (12), as shown in FIG. 1. In other embodiments, the agent may be delivered via the wall of one or more inflatable balloons. It yet further embodiments, the agent may be delivered via a needle used alone, or in combination with one or more inflatable balloons. It is understood that the agent delivery devices are not limited to what is described above and any other suitable device may be used in accordance with the present invention.

The system (10) also includes at least one first sensor (18) that measures pressure of the therapeutic and/or diagnostic agent being delivered via the port (16) in the catheter (12). Any suitable sensor type may be used in accordance with the present invention. As shown in FIG. 1, the sensor (18) may be positioned at the fluid source (14), at a particular location in the catheter lumen, and/or at the port (16). More than one sensor (18) may also be used, if desirable, and the sensors may be positioned at various locations, including those illustrated in this figure.

The system (10) further includes at least one second sensor (20) that measures at least one fluid dynamic characteristic of a patient. Again, any type of suitable sensor may be used, depending on what characteristic is being measured. The fluid dynamic characteristics of the patient include at least one of fluid velocity, fluid pressure, fluid density, and fluid temperature. It may be desirable to measure the fluid dynamic characteristics of the following bodily fluids: lymphatic fluid, blood, cerebrospinal fluid, interstitial fluid, and intracellular fluid. In one advantageous embodiment, the fluid dynamic characteristic of the patient being measured includes hemodynamics of the patient that can be measured by at least one of a finger sensor, near infrared sensor, and blood pressure cuff.

One or more first sensors (18) and one or more second sensors (20) are connected to a processor (22). The processor may be incorporated into the fluid source (14) or may be a separate device connected to the fluid source via a cable or wireless connection. The sensors (18) and (20) may likewise be connected to the processor (22) via a cable or wireless connection. The processor (22) receives and processes the measured pressure of the agent being delivered and the at least one fluid dynamic characteristic of the patient. Based on these measurements, the processor (22) then adjusts the delivery of the therapeutic and/or diagnostic agent. This way, the delivery of the agent is controlled and regulated by monitoring and taking into account one or more vital signs of the patient, such as body temperature, heart rate, blood pressure, and respiratory rate. For example, in certain applications, it will be desirable to know the degree to which the lung is inflated at any given time in order to deliver a therapeutic and/or diagnostic agent at the right time. In other cases, it is desirable to measure the systolic and diastolic blood pressure, and at appropriate times, apply a pressure that exceeds the systolic pressure in order to facilitate absorption of the agent into target tissue.

In some embodiments, the processor (22) also includes a display for displaying the data to the user and a user interface for the user's control of the operation of the device. In additional embodiments, the catheter (12) includes a data device, which may, for example, be optical, RFID, flash memory, etc. As a result, the fluid source (14) is able to identify the type of catheter that is connected and read catheter characterization data (including pressure, volume, dimensions, etc.) included thereon, and then adjust its control accordingly based on user input.

The delivery of the agent to tissue based on the measured characteristics may be adjusted in various ways. In some embodiments, the processor (22) adjusts the delivery of the therapeutic and/or diagnostic agent by increasing or decreasing pressure at which the agent is delivered via the port (16). In additional embodiments described in more detail below, one or more inflatable balloons may be used to adjust the delivery of the agent by increasing or decreasing a pressure exerted on a tissue wall.

The system (10) may also include an imaging device (not shown) disposed in one of the lumens of the catheter (12) to facilitate positioning of the catheter (12) at the proper location. For example, the lumen that delivers the therapeutic and/or diagnostic agent may be large enough to also accommodate the imaging device, such that the imaging device can exit the port (16), through which the agent is delivered to tissue. In other embodiments, the imaging device extends out of the opening at the distal end of the catheter (12), such that the tissue in front of the catheter can be viewed by the imaging device during the insertion of the catheter into a bodily cavity. In additional embodiments, the distal end of the catheter (12) has a transparent membrane made out of any suitable material. The imaging device is extended through one of the lumens of the catheter to the membrane, which allows for visualization of the area ahead of the catheter (12).

The imaging device can be any device suitable for viewing the target area, such as a coherent fiber bundle or appropriate optical element and lens assembly in conjunction with an imaging sensor (e.g., CMOS, CCD), having a sufficiently small outer diameters, such as, for example, 0.75 mm-1.5 mm. In some cases, the imaging device has a pre-shaped distal tip that enables it to easily extend through one of the aforementioned openings. The distal tip of the imaging device is preferably flexible such that it can be translated linearly or rotationally thereby allowing for 360° visualization of the surrounding area. The imaging device may also include an illumination source, such as LED or any other suitable illumination source, for illuminating tissue being viewed by the imaging device.

Figure 2:
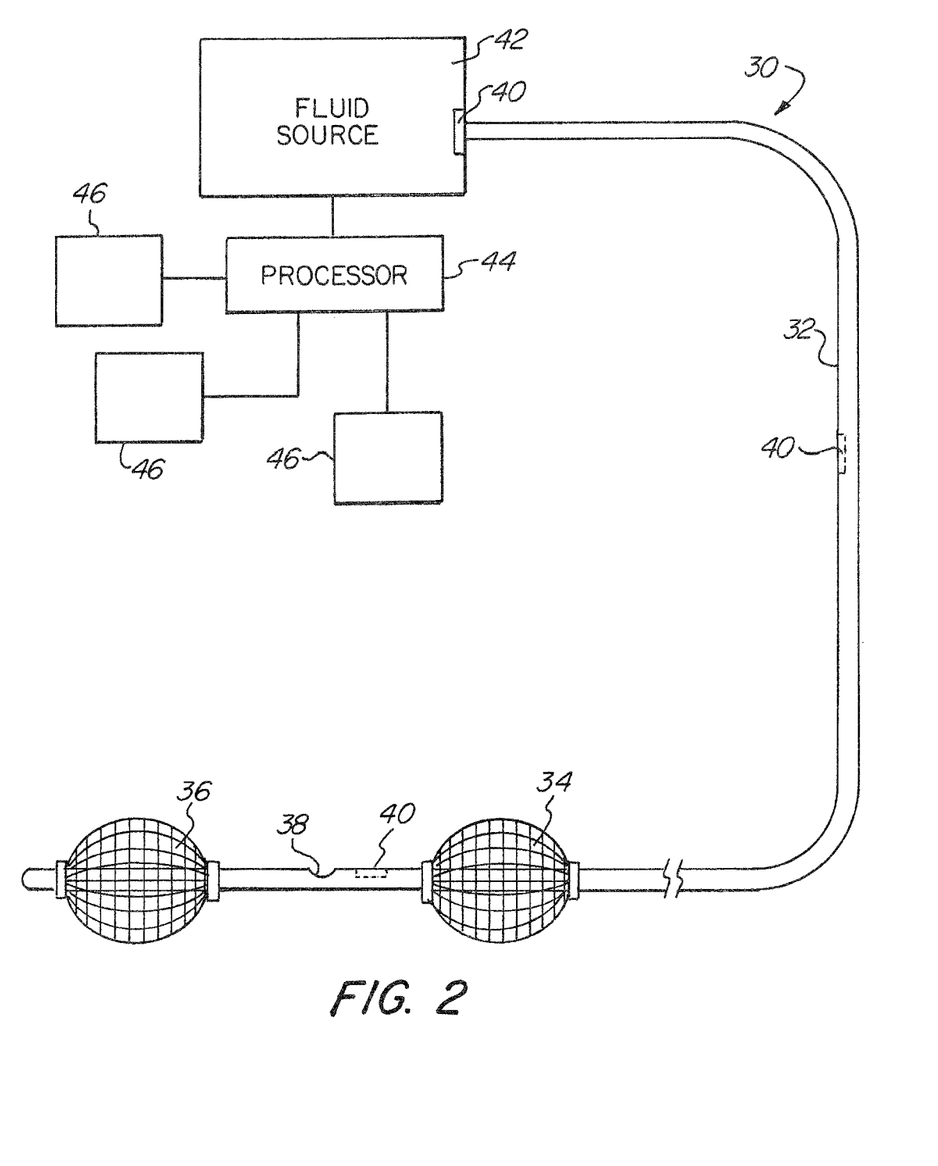
FIG. 2 is a schematic view of the system of FIG. 1, using a multi-balloon construct.

FIG. 2 illustrates an advantageous embodiment of the system of the present invention. In this embodiment, the catheter (32) has a proximal balloon (34) and a distal balloon (36) positioned near a distal end of the catheter (32). The balloons (34) and (36) may be made of latex, Yulex, polyethylene, nylon or other suitable material, and may come in a variety of sizes and diameters, which allow the catheter system (30) to be used in bodily cavities of various diameters and dimensions.

In some embodiments, one or both of the proximal and distal balloons (34) and (36) has a wall with an outer surface that comprises a textured surface intended to act as a gripping surface for attachment to bodily tissues to anchor the balloons at a target tissue site. The textured outer surface of the balloons (34) and (36) may be formed by a fiber mesh affixed to the surface of the balloons during or after the molding process. The fiber mesh may be made of elastane, lycra, polyurethane, nylon, nylon coated with other materials such as cotton, composite springs, or other appropriate material. In other embodiments, dimensional surface structures or inflatable sinuses that are encapsulated in the surface substrate of the balloons (34) and (36) may be used to produce the surface protrusions. The protrusions forming the textured surface can have various shapes and configurations, depending on a particular application.

The catheter (32) has a first lumen for inflation of the proximal balloon (34) and a second lumen for inflation of the distal balloon (36). It is understood that the proximal and distal balloons (34) and (36) may be inflated via the same catheter lumen. In use, after the catheter (32) is positioned adjacent the target tissue site, the proximal and distal balloons (34) and (36) are inflated via the fluid source (42) in sequence or simultaneously to create a fluidly isolated chamber between the balloons. The chamber functions to isolate the target treatment site from the surrounding tissue, which is particularly desirable during delivery of highly toxic chemotherapy agents to decrease exposure to such agents.

The balloons (34) and (36) or the catheter (32) or both may include imaging markers, such as radio opaque rings, located at or near the ends thereof. Such markers can be selected and appropriately positioned in order to reflect the relevant waves of various imaging modalities (e.g., x-ray) in order to allow the use of such modalities to assist with the precise positioning of the catheter and the balloons within a bodily cavity. Similarly, the balloons and/or the catheter may include a radiopaque material to facilitate positioning in a bodily cavity.

After the balloons (34) and (36) are inflated, the therapeutic and/or diagnostic agent is delivered to the chamber via a port (38) positioned between the proximal and distal balloons. In some advantageous embodiments, the agent is delivered via a plurality of ports positioned along the catheter (32) between the proximal and distal balloons (34) and (36). In additional advantageous embodiments, the agent is delivered via one or more openings in the wall of the proximal balloon (34) and/or distal balloon (36). The catheter (32) may have one or more agent delivery lumens to allow for sequential and/or simultaneous delivery of various agents.

Similar to the embodiment described above in connection with FIG. 1, the catheter (32) includes one or more first sensors (40) that measure the pressure at which the agent is delivered to the chamber. The sensors (40) may be positioned inside the chamber between the proximal and distal balloons (34) and (36), at the fluid source (42), and/or at any location in the catheter lumen. More than one sensor (40) may also be used, if desirable.

The catheter system further includes one or more second sensors (46) that measure one or more fluid dynamic characteristics of a patient, as described above in connection with FIG. 1. The data from the first sensor (40) and the second sensor (46) is sent to a processor (44), which processes the data and adjusts the delivery of the therapeutic and/or diagnostic agent based on this data. The delivery of the agent is adjusted by increasing or decreasing the pressure at which the agent is supplied to the fluidly isolated chamber between the proximal and distal balloons (34) and (36). This, in turn, changes volumetric pressure within the chamber to facilitate absorption of the agent into target tissue.

The catheter system also includes an outflow port and lumen for decreasing pressure inside the chamber between the proximal and distal balloons (34) and (36). The port (38) may be used as an outflow port, or an additional port positioned between the proximal and distal balloons may be provided for that reason. It is understood that the outflow port may be positioned at any desired location along the catheter. In additional embodiments, one or more outflow ports are provided in the wall of the proximal and/or distal balloons (34) and (36).

The outflow port is fluidly connected to a catheter lumen that functions to allow the therapeutic/diagnostic agent and/or air to flow out of the chamber and out of the catheter to decrease the pressure within the chamber. The lumen used for delivery of the agent may be used as an outflow lumen, or an additional lumen may be provided in the catheter (32) for that purpose. It is particularly important to be able to let the air out of the chamber between the balloons (34) and (36) to prevent embolism in a bodily lumen, in which this catheter system is being used.

In some advantageous embodiments, the outflow port and lumen supply vacuum from the fluid source (42) to the chamber between the proximal and distal balloons (34) and (36). This allows for faster decrease of the pressure inside the chamber, if desired.

Figure 3A:
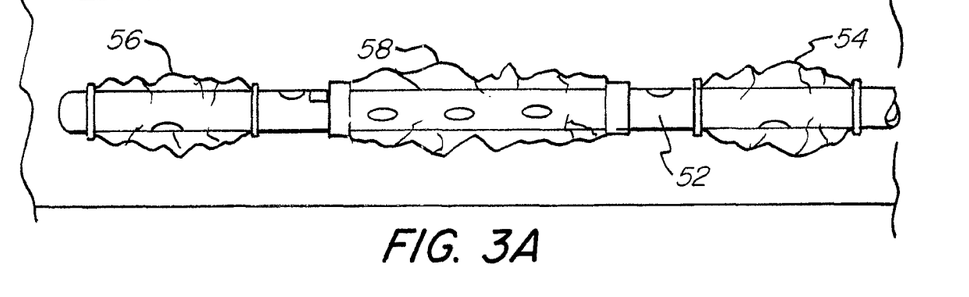
FIGS. 3A-3C are partially exposed, isometric views of the system of FIG. 2 with an additional multi-balloon construct, being operated in a bodily cavity.
Figure 3B:
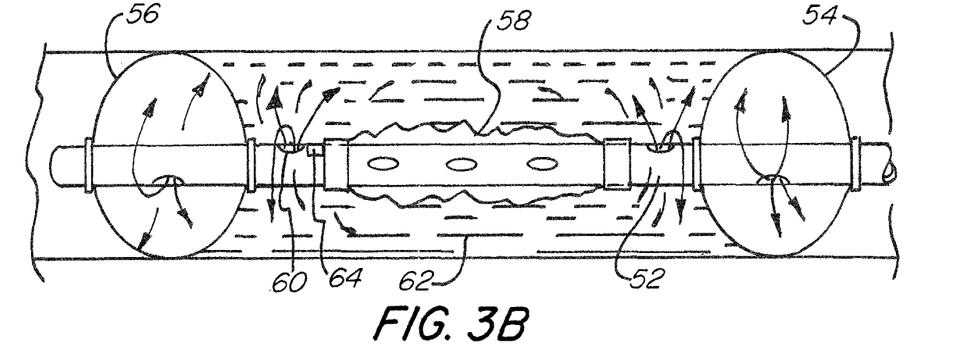
Figure 3C:
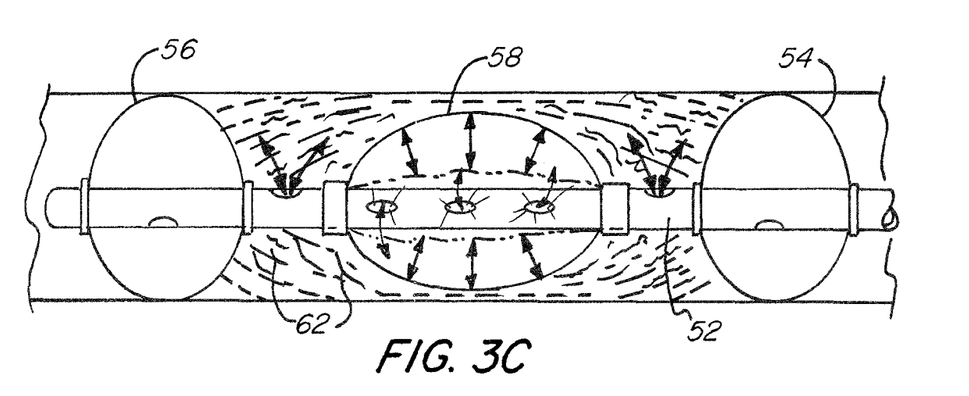

FIGS. 3A-3C illustrate an additional embodiment of the system of the present invention being used in a bodily cavity. In this embodiment, the catheter (52) includes a proximal inflatable balloon (54), a distal inflatable balloon (56) and a middle inflatable balloon (58) positioned between the proximal and distal balloons. The balloons may be made of any suitable material, as described above, and may come in a variety of sizes and diameters. In some advantageous embodiments, the middle balloon (58) has a wall with a textured outer surface intended to abrade bodily. The textured outer surface may be formed by a fiber mesh affixed to the surface of the balloon, or may comprise dimensional surface structures or inflatable sinuses that are encapsulated in the surface substrate of the balloon.

The textured outer surface of the balloon (58) functions to abrade bodily tissues. The abrasion of the bodily tissues stimulates bleeding and instigates flow of white blood cells, i.e. leukocytes, out of the circulatory system towards the site of tissue damage. This process, together with the adjustment of the delivery of the agent based on measurement of one or more fluid dynamic characteristics of a patient, facilitates absorption of the diagnostic and/or therapeutic agents into the adjacent tissues. The middle balloon (58) may be repeatedly inflated and deflated by the fluid source in pulsed fashion to gradually abrade tissue. The proximal and distal balloons (54) and (56) may also have a textured outer surface, which is used to abrade tissue and/or acts as a gripping surface for attachment to bodily tissues to anchor the balloons at a target tissue site.

As shown in FIG. 3A, the catheter (52) is first inserted into a bodily cavity, with the balloons in a deflated state. Then, as shown in FIG. 3B, the proximal and distal balloons (54) and (56) are inflated by supplying fluid to the balloons via a fluid source to create a fluidly isolated chamber (62) between the balloons. The proximal and distal balloons (54) and (56) may be inflated simultaneously or sequentially. Next, the therapeutic and/or diagnostic agent is delivered to the chamber (62) via one or more ports (60) positioned on the catheter between the proximal and distal balloons (54) and (56). It is noted that the agent may also be delivered through one or more openings in the wall of the middle balloon (58) and/or the wall of the proximal balloon (54) and the distal balloon (56). It is understood that any suitable method of delivering the agent to the chamber may be used in accordance with the present invention.

One or more first sensors (64) positioned in the chamber (64) and/or in the catheter lumen and/or at the fluid source measure the pressure of the agent being supplied to the chamber (62). The first sensor (64) positioned in the chamber (60) also measures volumetric pressure within the chamber (60) once it is filled with the agent. The measured data is then transmitted to a processor for processing.

Next, data from at least one second sensor positioned on a patient is measured and transmitted to the processor. As described above, at least one second sensor measures at least one fluid dynamic characteristic of a patient, including fluid velocity, fluid pressure, fluid density, and fluid temperature. Fluid dynamic characteristics of various bodily fluids, such as lymphatic fluid, blood, cerebrospinal fluid, interstitial fluid, and intracellular fluid, may be measured depending on a type of tissue the agent is being delivered to.

This measured fluid dynamic characteristic data is processed by the processor, which then adjusts the delivery of the therapeutic and/or diagnostic agent based on the measured volumetric pressure in the chamber (62) and the at least one fluid dynamic characteristic of the patient. The delivery may be adjusted by increasing or decreasing the pressure at which the agent is supplied to the chamber and/or by delivering more agent to the chamber, as described above. In some embodiments, the fluid dynamic characteristic data and volumetric pressure in the chamber are monitored continuously and the delivery of the agent is adjusted continuously. In additional embodiments, the data is measured and analyzed in cycles and the delivery of the agent is adjusted cyclically. In further advantageous embodiments, the system is capable of monitoring and data and adjusting the delivery of the agent both cyclically and continuously, as desired.

As shown in FIG. 3C, the delivery may also be adjusted by adjusting the inflation of the middle balloon (58). As the middle balloon (58) is inflated and deflated, the fluid pressure inside the chamber (62) is increased and decreased respectively. The first and second sensors continuously monitor the pressure of the agent and fluid pressure within the chamber, together with the fluid dynamic characteristics of the patient, and continuously adjust the delivery of the agent to tissue. This allows for agent delivery adjustments based on changing fluid dynamics of the patient and facilitates more efficient and precise delivery of the agent.

The inflation of the middle balloon (58) having an abrasive outer surface may also causes abrasion of surrounding tissue, which stimulates bleeding and instigates flow of white blood cells out of the circulatory system towards the site of tissue damage. This process, together with the adjustment of the delivery of the agent based on measurement of one or more fluid dynamic characteristics of a patient, facilitates absorption of the diagnostic and/or therapeutic agents into the adjacent tissues. The middle balloon (58) may be inflated and deflated repeatedly in a pulsed fashion to gently abrade the tissue and/or facilitate extravasation of the agent into the tissue, as set forth in U.S. Pat. Nos. 8,540,667 and 8,597,239 to Gerrans et al., the specifications of which are incorporated herein in their entirety.

Any of various agents useful in therapeutic application can be delivered in the above described manner. For example, the agent may comprise one or more chemical or biological drugs with useful pharmacological properties, as well as any other medicaments or other substances with medicinal or other therapeutic uses. Such agents may be synthetic or natural, so long as they have an advantageous therapeutic effect that can obtained by delivering the agent to a target site. In certain embodiments, agents particularly useful for chemotherapies, radiation therapies, or immunotherapies are delivered as described above.

Various agents may also be employed to assist in making diagnostic observations or monitoring procedures. For example, in some advantageous embodiments, the above described system may be used to deliver a contrast agent that allows or improves visualization via one or imaging modalities, which can be used to image the extravasation of the agent into the surrounding tissues throughout the course of a procedure. Such agents may include, for example, radiocontrast agents, such as iodine or barium, to improve X-ray based imaging techniques; MRI contrast agents, such as gadolinium, to improve magnetic resonance imaging; and microbubble contrast agents, to improve ultrasound imaging.

In some advantageous embodiments, biomarkers are used together with a therapeutic agent to observe and monitor the extravasation of the agent into the surrounding tissues. In some of these advantageous embodiments, CF3PM & MTFN-1 fluorinated radio-opaque biomarkers are used. The biomarkers may be detected by various non-invasive imaging modalities, such as X-Ray, MRI, CT, ultrasound, spectroscopy, etc.

With the addition of an appropriate inert dye or contrast media (e.g., radioactive, polarized, florescent, temperature sensitive) to a drug to be extravasated, the drug infusion rate and the amount of drug infused into the tissue can be monitored, quantified, and recorded/displayed, such as, for example, by capturing and storing sequential video frames under different illumination conditions (UV, IR, polarized, color filters, etc.). Further, by deploying a contrast agent along with a therapeutic agent, one can visually identify the extravasation depths and/or discern the requisite volumetric pressure, force, temperature, frequency and/or time to achieve efficacious delivery of the therapeutic agent to the desired depth of penetration at the intended treatment site.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

The invention claimed is:

1. A system for delivering a therapeutic and/or diagnostic agent to tissue, comprising:
   a catheter having a delivery port and a lumen through which a therapeutic and/or diagnostic agent is communicated to the delivery port;

at least one first sensor that measures pressure of the therapeutic and/or diagnostic agent being delivered via said port and generates a signal indicating the pressure;

a processor that receives the signal from said at least one first sensor; and at least one second sensor that measures at least one fluid dynamic characteristic of a subject and transmits a signal indicating the at least one fluid dynamic characteristic to said processor;

wherein said processor adjusts the delivery of the therapeutic and/or diagnostic agent based at least in part on said measured pressure of the agent and said at least one fluid dynamic characteristic of the subject.

2. The system of claim 1, wherein said at least one fluid dynamic characteristic of the subject comprises at least one of diastolic pressure and systolic pressure.

3. The system of claim 1, wherein said at least one fluid dynamic characteristic of the subject comprises a lymphatic fluid dynamic characteristic.

4. The system of claim 1, wherein said at least one fluid dynamic characteristic of the subject comprises a blood dynamic characteristic.

5. The system of claim 1, wherein said at least one fluid dynamic characteristic of the subject comprises cerebrospinal fluid dynamic characteristic.

6. The system of claim 1, wherein said at least one fluid dynamic characteristic of the subject comprises an interstitial fluid dynamic characteristic.

7. The system of claim 1, wherein said at least one fluid dynamic characteristic of the subject comprises an intracellular fluid dynamic characteristic.

8. The system of claim 1, wherein said at least one fluid dynamic characteristic of the subject comprises at least one of fluid velocity, fluid pressure, fluid density, and fluid temperature.

9. The system of claim 1, further comprising a fluid source, wherein the at least one first sensor is positioned at said fluid source.

10. The system of claim 1, wherein the at least one first sensor is positioned in a catheter lumen.

11. The system of claim 1, wherein the processor adjusts the delivery of the therapeutic and/or diagnostic agent by increasing or decreasing pressure at which the agent is delivered via the delivery port.

12. The system of claim 1, wherein said catheter comprises a proximal balloon and a distal balloon and a fluid source that inflates said proximal and distal balloons by supplying fluid thereto to create a chamber between the proximal and distal balloons, and wherein said delivery port is positioned between the proximal and distal balloons.

13. The system of claim 12, wherein the at least one first sensor is positioned inside the chamber between the proximal and distal balloons.

14. The system of claim 12, wherein the processor adjusts the delivery of the therapeutic and/or diagnostic agent by increasing or decreasing volumetric pressure inside said chamber.

15. The system of claim 12, wherein said catheter further comprises a middle balloon positioned between the proximal and distal balloons and wherein the processor adjusts the delivery of the therapeutic and/or diagnostic agent by adjusting the inflation of the middle balloon.

16. The system of claim 12, wherein said catheter further comprises an outflow lumen that allows fluid to escape said chamber.

17. A method of delivering a therapeutic and/or diagnostic agent to tissue, comprising the steps of:
inserting a catheter into a bodily cavity;
delivering the therapeutic and/or diagnostic agent to tissue via said catheter;
measuring pressure at which the therapeutic and/or diagnostic agent is delivered to tissue;
measuring at least one fluid dynamic characteristic of a subject; and
adjusting the delivery of the therapeutic and/or diagnostic agent based at least in part on said measured pressure of the agent and said at least one fluid dynamic characteristic of the subject.

18. A method of delivering a therapeutic and/or diagnostic agent to tissue, comprising the steps of:
inserting a catheter into a bodily cavity, said catheter comprising a proximal balloon and a distal balloon;
inflating the proximal and distal balloons to create a chamber between the proximal and distal balloons;
delivering the therapeutic and/or diagnostic agent to said chamber;
measuring fluid pressure in said chamber;
measuring at least one fluid dynamic characteristic of a subject; and
adjusting the delivery of the therapeutic and/or diagnostic agent based at least in part on said measured fluid pressure in said chamber and said at least one fluid dynamic characteristic of the subject.

* * * * *